United States Patent [19]

Boutet et al.

[11] Patent Number: 5,065,866

[45] Date of Patent: Nov. 19, 1991

[54] STORAGE PHOSPHOR CASSETTE ASSEMBLY

[75] Inventors: John C. Boutet, Rochester, N.Y.; Gary R. Unruh, Newark, Calif.

[73] Assignees: Eastman Kodak Company, Rochester, N.Y.; Lumisys, Sunnyvale, Calif.

[21] Appl. No.: 617,121

[22] Filed: Nov. 21, 1990

[51] Int. Cl.⁵ .............................................. G03B 42/04
[52] U.S. Cl. ................................ 206/455; 378/182; 250/327.2; 250/484.1
[58] Field of Search .............. 206/455; 378/182, 183, 378/184, 185, 186, 187; 250/484.1 R, 484.1 B, 327.2 A

[56] References Cited

U.S. PATENT DOCUMENTS

| Re; 31,847 | 3/1985 | Luckey | 250/327.2 |
|---|---|---|---|
| 4,295,565 | 10/1981 | Takeuchi | 206/455 |
| 4,663,528 | 5/1987 | Fujiwara et al. | 250/327.2 A |
| 4,738,366 | 4/1988 | Schmidt et al. | 206/455 X |
| 4,802,618 | 2/1989 | Seto et al. | 206/455 X |
| 4,810,874 | 3/1989 | Torii | 378/185 X |
| 4,816,369 | 3/1989 | Matsuda et al. | 250/327.2 A X |
| 4,827,136 | 5/1989 | Bishop, Jr. et al. | 378/182 X |
| 4,849,630 | 7/1989 | Fukai et al. | 250/484.1 B X |
| 4,889,233 | 12/1989 | Torii | 378/182 X |
| 4,961,000 | 10/1990 | Finbenzeller et al. | 250/484.1 B |
| 4,987,308 | 1/1991 | Tamura et al. | 378/187 X |

Primary Examiner—Paul T. Sewell
Assistant Examiner—Jacob K. Ackun, Jr.
Attorney, Agent, or Firm—William F. Noval

[57] ABSTRACT

A storage phosphor cassette assembly includes a rectangular cassette and a photo-stimulable storage phosphor mounted on a rigid plate removably positioned within the cassette. The rectangular cassette is closed on five sides and has a side opening which is closed off by a rib on the end of the storage phosphor plate. The cassette and rib are configured to provide a light lock to prevent undesirable exposure of the storage phosphor.

3 Claims, 4 Drawing Sheets

STORAGE PHOSPHOR CASSETTE ASSEMBLY

BACKGROUND OF THE INVENTION

1. Technical Field

This invention relates to photo-stimulable storage phosphor apparatus and more particularly to a storage phosphor cassette assembly having a light lock to prevent undesirable light from exposing the storage phosphor.

2. Background Art

In a photo-stimulable storage phosphor imaging system, as described in U.S. Pat No. Re. 31,847 reissued March 12, 1985 to George W. Luckey, a photo-stimulable phosphor sheet is exposed to an imagewise pattern of short wavelength radiation, such as X-radiation, to record a latent image pattern in the photo-stimulable phosphor sheet. The latent image is read out by stimulating the phosphor with a relatively long wavelength stimulating radiation, such as red or infrared light. Upon stimulation, the photo-stimulable phosphor releases emitted radiation of an intermediate wavelength, such as blue or violet light, in proportion to the quantity of short wavelength radiation that was received. To produce a signal useful in electronic image processing, the photo-stimulable phosphor sheet is scanned in a raster pattern by a beam of light produced, for example, by a laser deflected by an oscillating or rotating scanning mirror, and the emitted radiation is sensed by a photodetector such as a photomultiplier tube to produce the electronic image signal.

In applications in which the photo-stimulable storage phosphor sheet is exposed to X-radiation at one location and read out at another location, it is desirable that the photo-stimulable storage phosphor sheet not be exposed to undesirable light to prevent image degradation. It is also desirable that the storage phosphor sheet be protected from damage during handling between the exposure and read out stations.

SUMMARY OF THE INVENTION

According to the present invention, there is provided a storage phosphor cassette assembly including a rectangular cassette and a photo-stimulable storage phosphor mounted on a rigid plate removably positioned within the cassette. The rectangular cassette is substantially closed on five sides and has a side opening which is closed off by a rib on an end of the storage phosphor plate.

According to a feature of the present invention, the cassette and storage phosphor plate rib are configured to provide a light lock to prevent undesirable exposure of the storage phosphor.

BRIEF DESCRIPTION OF THE DRAWINGS

The invention is described with reference to the accompanying drawings wherein like elements are numbered with like numbers.

DESCRIPTION OF THE PREFERRED EMBODIMENTS

Figure 1:
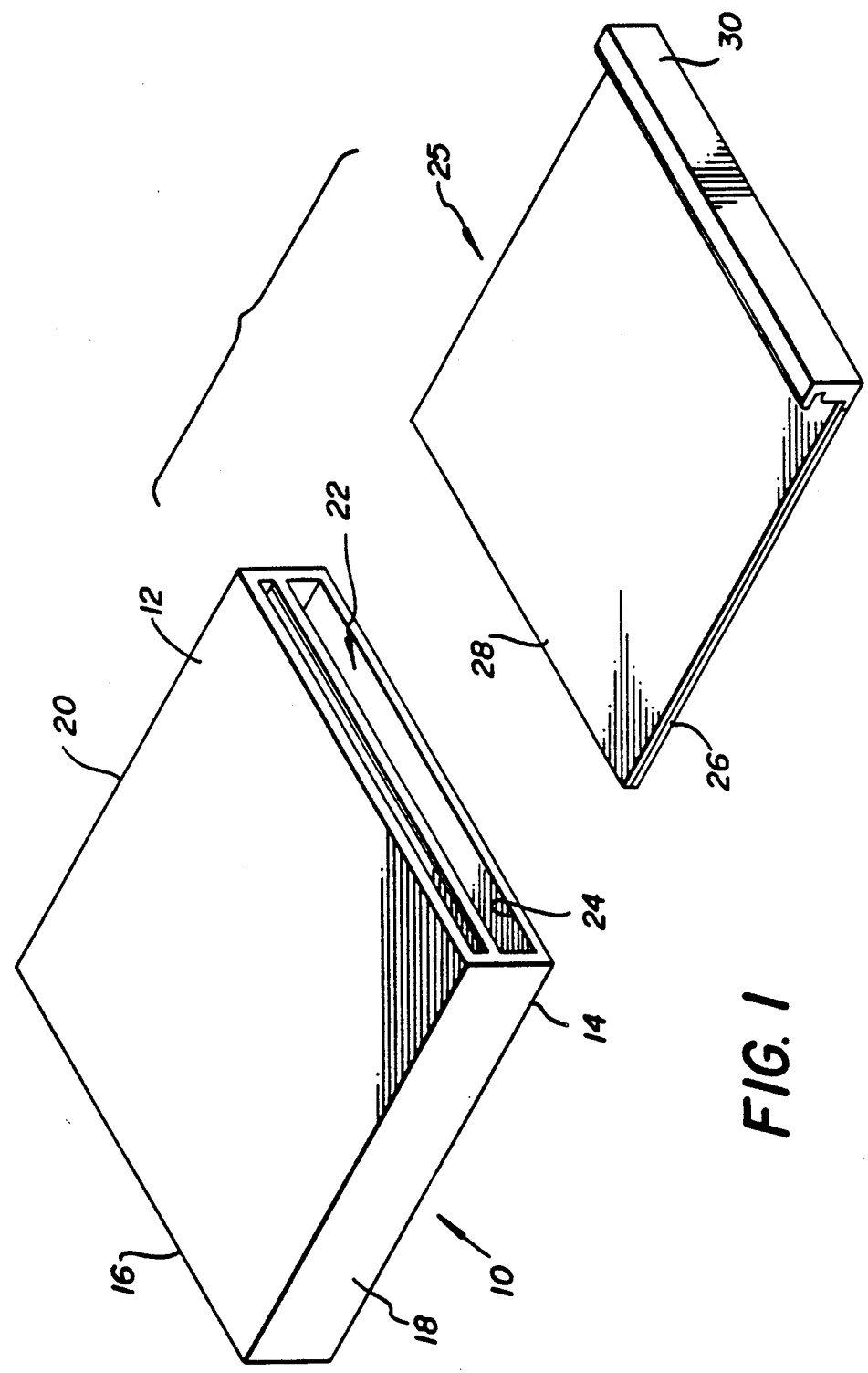
FIG. 1 is a perspective view of one embodiment of the present invention.

Referring now to FIG. 1, there is shown an embodiment of the present invention. As shown, a photo-stimulable storage phosphor cassette assembly includes a substantially rectangular cassette 10 having spaced, elongated rectangular upper and lower walls 12 and 14, end wall 16 and spaced side walls 18 and 20. Walls 12, 14, 16, 18, and 20 form a five sided structure having a cavity 22 with an open end 24. Storage phosphor plate 25 includes an elongated rectangular rigid member 26 supporting photo-stimulable storage phosphor 28. Plate 26 has upstanding rib 30. Storage phosphor plate 25 is removably positioned in cavity 22 of cassette 10, such that rib 30 closes off opening 24.

Cassette 10 and plate 25 have interlocking light lock structure to prevent exposure of storage phosphor 28 to light. Thus image degradation is minimized to a latent image stored in storage phosphor 28. The light lock structure is shown more clearly in FIG. 2. As shown, end 32 of upper wall 12 of cassette 10 has a slot 34 between end segments 36 and 38. Rib 30 of plate 25 has a slot 42 for receiving end segment 38 of wall 12 and has a segment 44 which projects into slot 34 in wall 12. Segments 36, 38 and 44 are preferably bevelled (as at 36a, 38a and 44a) to facilitate insertion and removal of plate 25 from cassette 10. The interlocking engagement of rib 30 with wall 12 prevents wall 12 from bowing up and from letting light to leak into phosphor 28.

Figure 2:
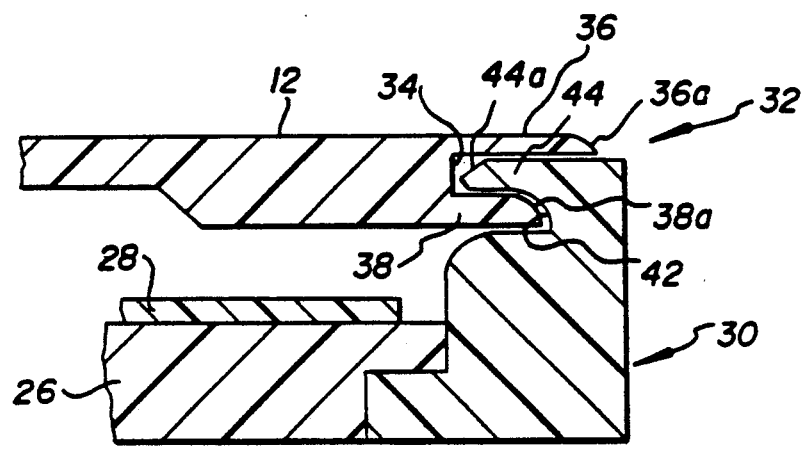
FIG. 2 is a partially sectional elevational view showing details of the light lock structure of the embodiment of FIG. 1.

As shown in FIG. 2, rib 30 is a separate piece mounted on the end of plate 26 by suitable means (such as screws). It will be understood that rib 30 may be formed integral with plate 26.

Figure 3:
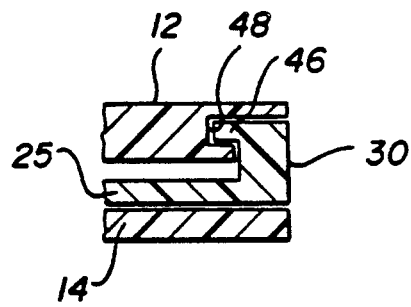
FIGS. 3, 4 and 5 are partially sectional, elevational views of other embodiments of the present invention.
Figure 4:
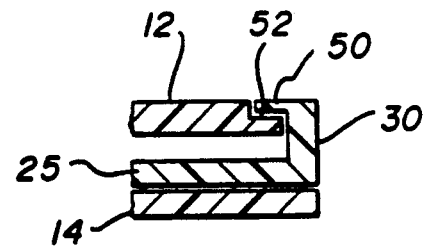
Figure 5:
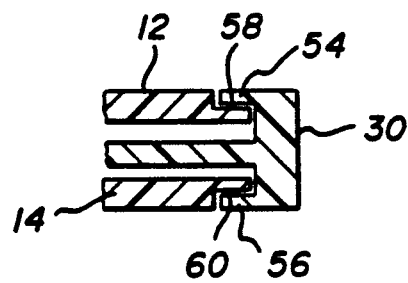

Referring now to FIGS. 3, 4 and 5, there are shown further embodiments of the present invention. In FIG. 3, rib 30 of plate 25 has a lip 46 which engages slot 48 in the end of wall 12. In FIG. 4, rib 30 of plate 25 has a lip 50 which engages recessed portion 52 of wall 12. In FIG. 5, rib 30 has respective upper and lower lips 54 and 56 which engage respective recessed portions 58 and 60 of walls 12 and 14. In each of these embodiments, the engaging structure of plate 25 and cassette 10 provide a light lock to prevent unwanted light from leaking to the storage phosphor plate.

Figure 6:
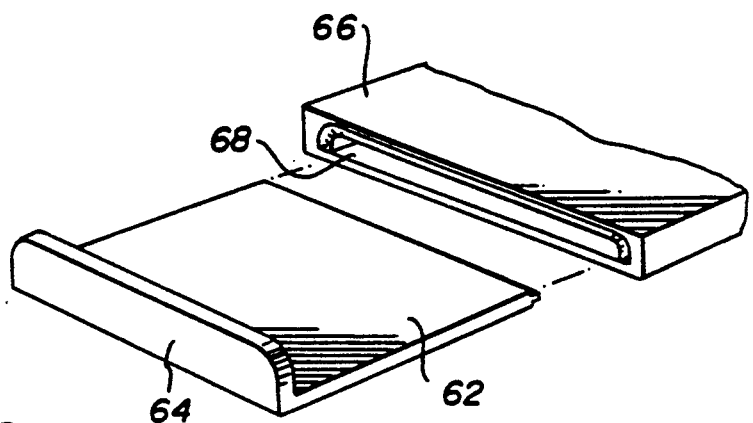
FIGS. 6 and 7 are perspective views and FIG. 8 is a partially sectional, elevational view of another embodiment of the present invention.
Figure 7:
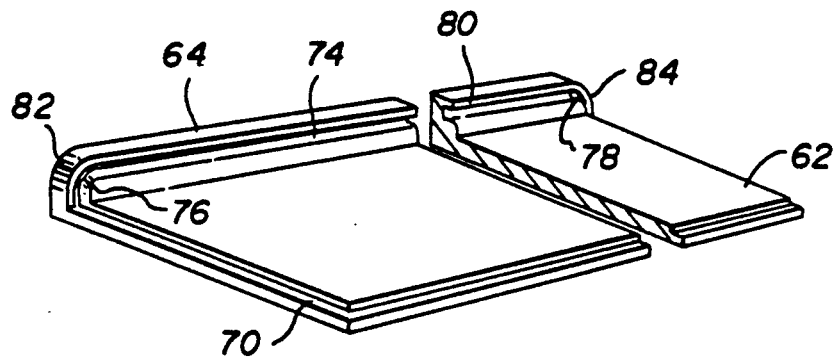
Figure 8:
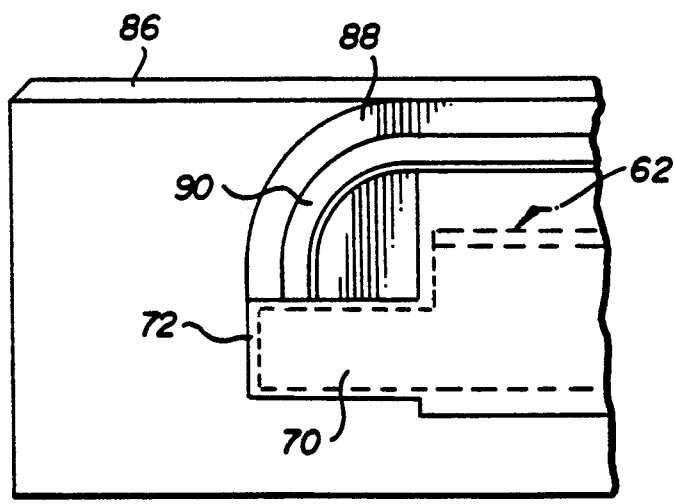

As shown, in FIGS. 6, 7 and 8, another embodiment of the present invention includes light lock structure extending to the sides of the storage phosphor. Storage phosphor plate 62 has a rib 64 with rounded ends and is removably positioned in cavity 68 of cassette 66 (FIG. 6). Plate 62 (FIG. 7) has a peripheral ledge 70 which mates with a lower slot 72 (FIG. 8) in the side and end walls of cassette 66. Rib 64 has a slot 74 with downwardly extending sides 76 and 78 and bounded by lip 80 with downwardly extending sides 82 and 84. The open end 86 of cassette 66 (FIG. 8) includes a light trap slot 88 configured to receive lip 80 of plate rib 64 and a lip 90 which engages slot 74 of rib 64. The configuration of lips 64 and 90 and slots 74 and 88 are such as to prevent light from entering cassette 66 from the sides and the top of the rib end of storage plate 62.

Figure 9:
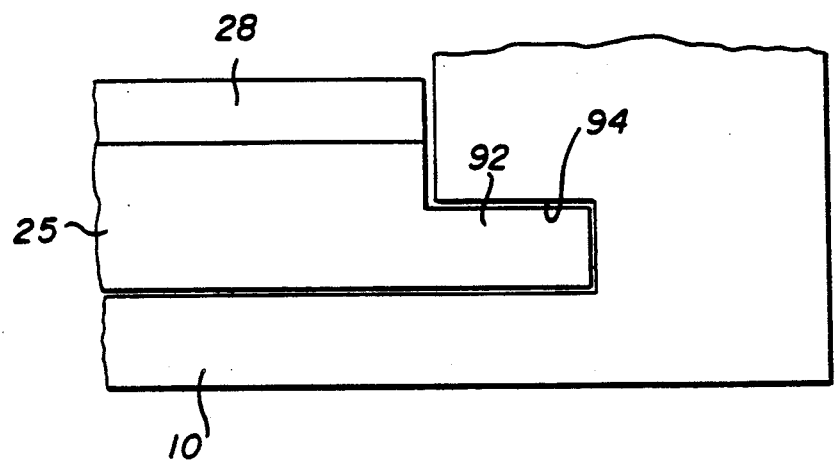
FIGS. 9 and 10 are partial, perspective views of still other embodiments of the present invention.
Figure 10:
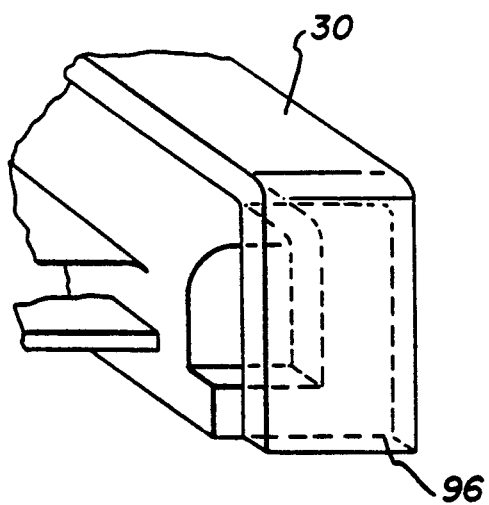

FIGS. 9 and 10 show further embodiments of the present invention. The embodiment of FIG. 9 is similar to the embodiment of FIG. 2, except plate 25 has a peripheral ledge 92 which mates with a peripheral slot 94 in cassette 10. FIG. 10 shows an enhanced light trap 96 on the side of rib 30.

The invention has been described in detail with particular reference to preferred embodiments thereof. But it will be understood that variations and modifications can be effected within the spirit and scope of the invention.

What is claimed is:

1. A photo-stimulable storage phosphor cassette assembly comprising:

a generally rectangular cassette having spaced, elongated rectangular upper and lower walls and an end wall and spaced side walls joining said upper and lower walls; wherein said upper and lower walls, said end wall and said side walls enclose a five-sided cavity having an open end;

an elongated, rectangular rigid plate supporting a photo-stimulable storage phosphor layer, said plate having an upstanding rib;

said plate being dimensioned to be removably positioned in said cassette cavity so that said rib closes off said cassette open end; and complementary light lock means on said plate rib and said cassette for preventing light from leaking into said cavity when said cassette and storage phosphor plate are assembled together.

2. The assembly of claim 1 wherein said complementary light-lock means includes a lip on one of said plate rib and upper cassette wall and a complementary slot on the other of said plate rib and upper cassette wall.

3. The assembly of claim 1 wherein said complementary light-lock means includes a lip on said plate rib and a complementary recessed portion on said upper cassette wall.

* * * * *